United States Patent
Mullen et al.

(10) Patent No.: US 9,664,431 B2
(45) Date of Patent: May 30, 2017

(54) CRYOGENIC SAMPLE HOLDER

(71) Applicant: The World Egg Bank, Phoenix, AZ (US)

(72) Inventors: Steven F. Mullen, Phoenix, AZ (US); Daniel Ling, Phoenix, AZ (US); Justin Carland, Phoenix, AZ (US)

(73) Assignee: The World Egg Bank, Inc, Phoenix, AZ (US)

( * ) Notice: Subject to any disclaimer, the term of this patent is extended or adjusted under 35 U.S.C. 154(b) by 716 days.

(21) Appl. No.: 13/794,569

(22) Filed: Mar. 11, 2013

(65) Prior Publication Data
US 2013/0263622 A1    Oct. 10, 2013

Related U.S. Application Data

(60) Provisional application No. 61/609,748, filed on Mar. 12, 2012, provisional application No. 61/614,155, filed on Mar. 22, 2012.

(51) Int. Cl.
*F25D 3/08*    (2006.01)
*F25D 25/00*    (2006.01)
(Continued)

(52) U.S. Cl.
CPC .......... *F25D 11/003* (2013.01); *A01N 1/0268* (2013.01); *B01L 7/04* (2013.01);
(Continued)

(58) Field of Classification Search
CPC ..... F25D 3/14; B01L 7/04; B01L 7/50; B01L 9/06; B01L 9/065; B01L 2200/18;
(Continued)

(56) References Cited

U.S. PATENT DOCUMENTS 3,108,840 A    10/1963  Conrad et al.
4,314,450 A    2/1982   Pelloux-Gervais
(Continued)

FOREIGN PATENT DOCUMENTS

DE    102005041481    9/2006
EP    0181235    5/1986
(Continued)

OTHER PUBLICATIONS

Search Report for GB Invention Patent Application No. GB1409271.2; Jun. 13, 2014; p. 1.
(Continued)

*Primary Examiner* — Ryan J Walters
*Assistant Examiner* — Joseph Trpisovsky
(74) *Attorney, Agent, or Firm* — Jackson White, PC; Steven J. Laureanti

(57) ABSTRACT

The present disclosure describes a cryogenic vessel or holder designed to retain biological specimens, such as embryos or unfertilized eggs. The holder is insulated to reduce the rate of warming of the biological specimens, can hold numerous biological specimens snuggly to alleviate damage by jarring, and has an inner cavity that receives cryogen to keep the biological specimens immersed in cryogen during shipping. The design allows for safer shipping and handling of the biological specimens with less risk of damage. The design can also be utilized as a long-term sample holding and storage device.

23 Claims, 15 Drawing Sheets

(51) Int. Cl.
  *F25B 19/00* (2006.01)
  *F25D 17/02* (2006.01)
  *F25D 11/00* (2006.01)
  *B01L 9/06* (2006.01)
  *A01N 1/02* (2006.01)
  *B01L 7/04* (2010.01)
  *G01N 1/42* (2006.01)
  *B01L 7/00* (2006.01)

(52) U.S. Cl.
  CPC ............... *B01L 9/06* (2013.01); *B01L 9/065* (2013.01); *B01L 7/50* (2013.01); *B01L 2200/18* (2013.01); *B01L 2300/021* (2013.01); *B01L 2300/042* (2013.01); *B01L 2300/069* (2013.01); *B01L 2300/0609* (2013.01); *B01L 2300/0838* (2013.01); *B01L 2300/185* (2013.01); *B01L 2300/1883* (2013.01); *B01L 2300/1894* (2013.01); *G01N 1/42* (2013.01)

(58) Field of Classification Search
  CPC ....... B01L 2300/1894; B01L 2300/042; B01L 2300/0609; B01L 2300/0838
  USPC ...... 62/371, 62, 51.1, 64; 220/560.1, 560.12
  See application file for complete search history.

(56) References Cited

U.S. PATENT DOCUMENTS

| | | | |
|---|---|---|---|
| 4,883,644 A | 11/1989 | Perlman | |
| 4,955,480 A * | 9/1990 | Sexton | 206/528 |
| 5,008,084 A * | 4/1991 | Kelley | 422/547 |
| 5,934,099 A * | 8/1999 | Cook et al. | 62/457.2 |
| 7,608,224 B2 | 10/2009 | Degel et al. | |
| 2005/0016198 A1* | 1/2005 | Wowk et al. | 62/371 |
| 2005/0276729 A1* | 12/2005 | Helt | 422/102 |
| 2006/0162652 A1* | 7/2006 | Lang et al. | 118/429 |
| 2009/0202978 A1 | 8/2009 | Shaham | |

FOREIGN PATENT DOCUMENTS

| | | |
|---|---|---|
| EP | 2384702 | 11/2011 |
| WO | 2008028499 | 3/2008 |
| WO | 2011159934 | 12/2011 |

OTHER PUBLICATIONS

Search Report for GB Invention Patent Application No. GB1304414.4; Jul. 18, 2013; p. 1.
Examination Report for GB Invention Patent Application No. GB1304414.4; Aug. 1, 2014; pp. 1-2.

* cited by examiner

CRYOGENIC SAMPLE HOLDER

CROSS-REFERENCE TO RELATED APPLICATIONS

This application claims priority to U.S. Provisional Patent Application No. 61/609,748 filed Mar. 12, 2012, and also claims priority to U.S. Provisional Application No. 61/614,155 filed Mar. 22, 2012, the disclosures of which are incorporated herein in their entirety for all purposes.

TECHNICAL FIELD

This disclosure generally relates to cryogenic transfer of biological specimens such as tissue, embryos and unfertilized eggs, and more particularly, to transport vessels designed to keep specimens at a temperature at which they will maintain their viability.

BACKGROUND

A cryogenic transport vessel (or "sample holder" or "holder") allows a user to transfer samples of organic tissue. In known apparatuses for cryofixation or for cryopreparation, liquid nitrogen or other cryogen, such as liquid helium, is generally used as a coolant and is received in a cooling chamber of the vessel for this purpose. The cryofixation of specimens in the form of biomedical test samples or similarly conditioned physico-chemical test samples is usually carried out by inserting a holder having the specimens into a container of cryogen thereby cooling the specimens to below their glass transition temperature.

During cryotransfer, a specimen in the preferred embodiments herein is maintained at a temperature at or below −160 degrees Celsius to −100 degrees Celsius because the structure of the specimen would change at temperatures above this range, which could render the specimen unusable. In order to transfer the specimen transport vessel with minimal risk to the specimens, the vessel is usually filled with a cryogen so that the cryotransfer of the specimen vessel to another apparatus is conducted with the specimen immersed in the cryogen.

It is common for the cryogen in a vessel to be directly applied to biological specimens. This is usually accomplished by introducing the cryogen into the vessel through apertures, where the cryogen enters into a cavity, and wherein the specimens are in the cavity. Furthermore, once the vessel is removed from the cryogen bath in which it is immersed during shipping, the specimens begin to heat rapidly. A need therefore exists for an improved cryogenic sample holder.

SUMMARY

The present disclosure describes a sample holder designed to hold biological sample support devices (or "BSSDs") (such as straws, cryoleafs, and cryotops, among others, which are known in the art). BSSDs are commonly utilized in storing and transporting biological specimens, such as embryos or unfertilized eggs, in cryogen. The holder is designed to retain BSSDs in a manner that (1) reduces the rate of warming of biological specimens when the holder is removed from a container including cryogen, (2) reduce jarring or shaking that can occur during handling and transportation, and (3) hold and identify numerous biological specimens at the same time. The sample holder can also be utilized as a long-term holding and storage device.

A sample holder according to aspects of the invention stays colder for longer periods when removed from a shipping container containing cryogen because, among other reasons, it is more insulating than known devices. Further, the specimens are held more snuggly, and are less prone to being shaken or to strike another object, which could damage a biological specimen.

DETAILED DESCRIPTION OF PREFERRED EMBODIMENTS

The description set forth below in connection with the appended drawings is intended to describe presently preferred embodiments of the disclosure and is not intended to limit the scope of the claimed inventions.

Generally described, the present disclosure relates to a cryogenic sample holder (or "sample holder" or "holder"). FIGS. 1 through 9 describe a first sample holder according to a preferred embodiment.

Figure 1:
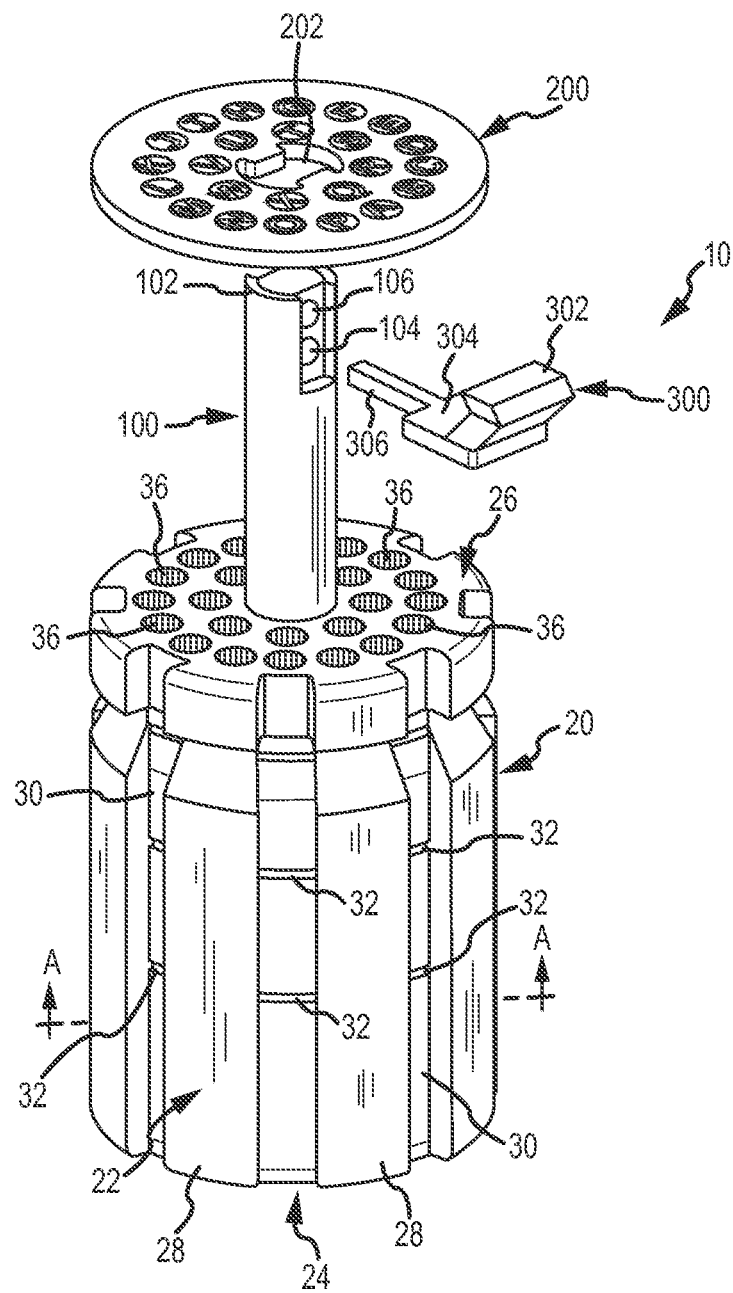
FIG. 1 is a perspective, front view of an exemplary cryogenic sample holder in accordance with one or more aspects of the present disclosure.
Figure 2:
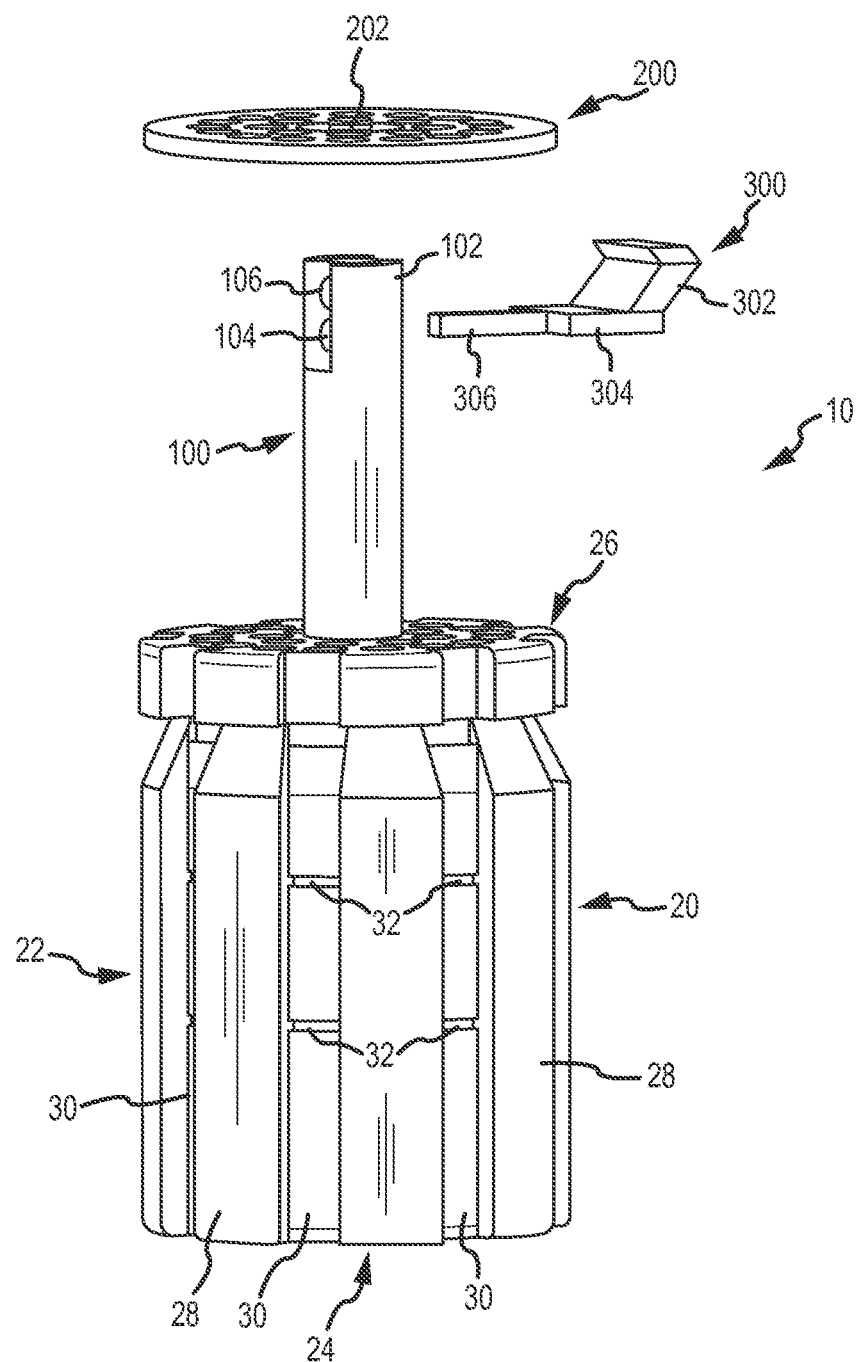
FIG. 2 is a side view of the exemplary cryogenic sample holder of FIG. 1.

Turning now to FIG. 1, an illustrative embodiment is shown. Holder 10 can include a number of inner cavities, and most preferably has one inner cavity, that receives cryogen. When holder 10 is removed from the cryogen solution, the interior cavity(ies) preferably retain at least part of the cryogen thus preserving the temperature of BSSDs within the holder.

Holder 10 comprises a body 20, a stem 100, a cap 200 and a pin 300. Body 20 is preferably comprised of an insulating material, which is most preferably a plastic that will not break when exposed to the cryogen. Polypropylenes, polyethylenes and polyvinyl chlorides may be suitable to form body portion 20.

Figure 9:
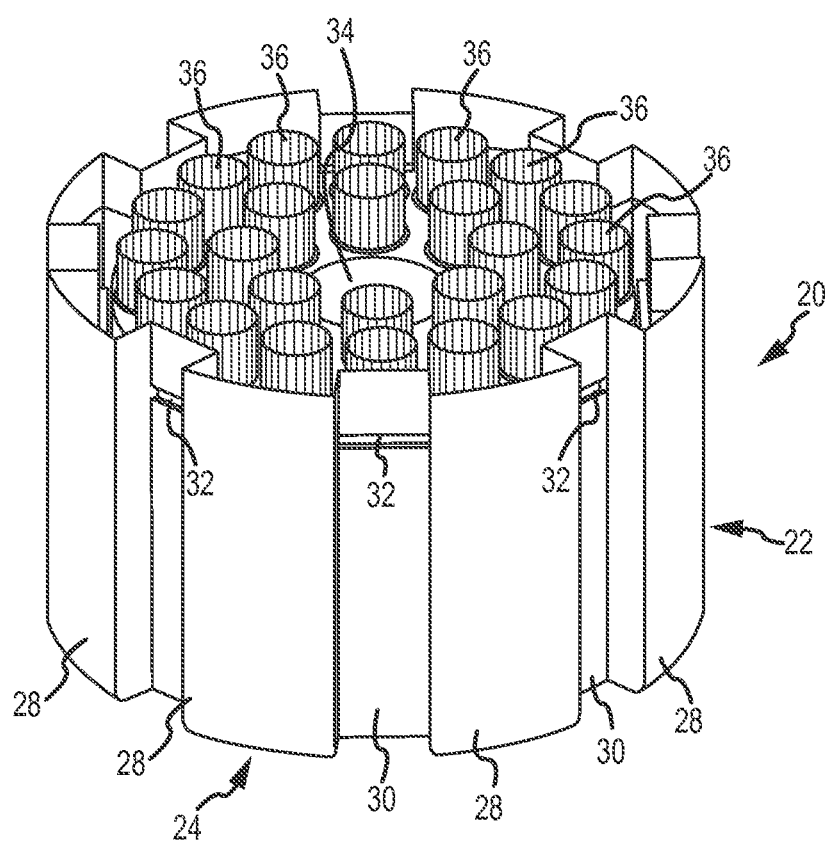
FIG. 9 is a side perspective view of a cross section of the exemplary cryogenic sample holder of FIG. 1.

As shown body portion 20 has an exterior side surface 22, a bottom surface 24 and a top surface 26. In this embodiment, side surface 24 has alternating projections 28 and channels 30. Projections 28 help to insulate body 20 and may either be solid or hollow. Channels 30 have openings 32 through which cryogen passes when body 20 is placed in cryogen. The cryogen passes through openings 32 and into inner cavity 34, as best seen in FIG. 9.

Optionally, if projections 28 are hollow one or more may have an opening that permits cryogenic fluid to enter the projection, which would assist in maintaining body 20 at a low temperature.

Further, the exterior side surface 22 may be smooth and cylindrical, but still include openings 32 through which cryogen can pass into inner cavity 34.

Bottom surface 24 is preferably generally flat and solid.

Top surface 26 includes one or more, and preferably a plurality of, openings 36. Openings 36 extend from the top surface 26 downward into inner cavity 34 wherein they are in the cryogen when cryogen is in inner cavity 34, as can best be seen in FIG. 9. Openings 36 may be closed at the bottom, in which case cryogen will not enter them, or may be open, in which case cryogen will enter them.

A stem 100 is preferably in the center of and extends upward from top surface 26. Stem 100 serves two purposes: (1) it is part of a structure to retain BSSDs when they are in the openings 36, and (2) it can be used to lift and move holder 10. As shown stem 100 is cylindrical and has a top 102 formed in the shape of a keyway, although any suitable shape will suffice.

The top 102 of stem 100 in this embodiment has two holes; a lower hole 104 and an upper hole 106. Stem 100 is preferably integrally formed with and is comprised of the same material as body 20.

Figure 3:
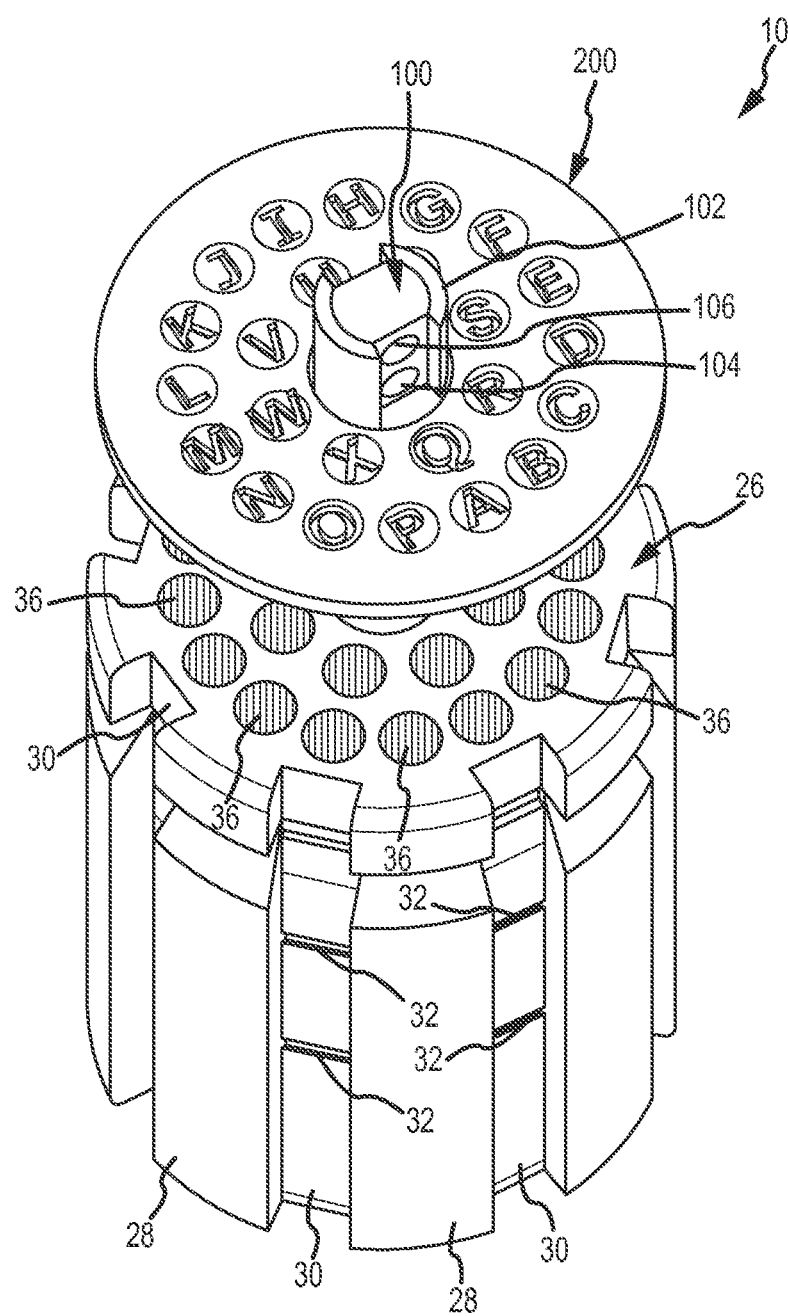
FIG. 3 is a front perspective view of the exemplary cryogenic sample holder of FIG. 1 with the cap on the stem and not showing the pin.
Figure 4:
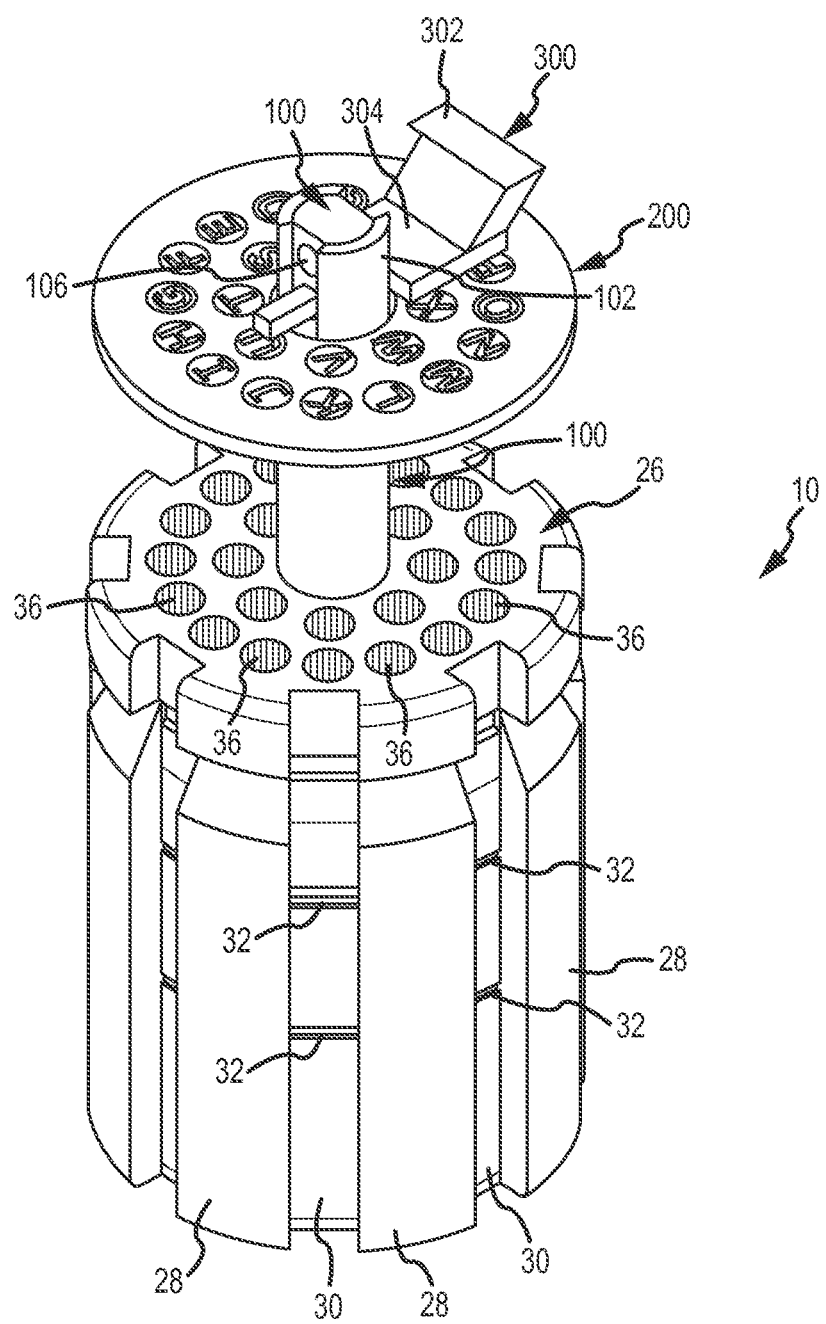
FIG. 4 is a front perspective view of the exemplary cryogenic sample holder of FIG. 3 with the pin positioned in an aperture of the stem.
Figure 5:
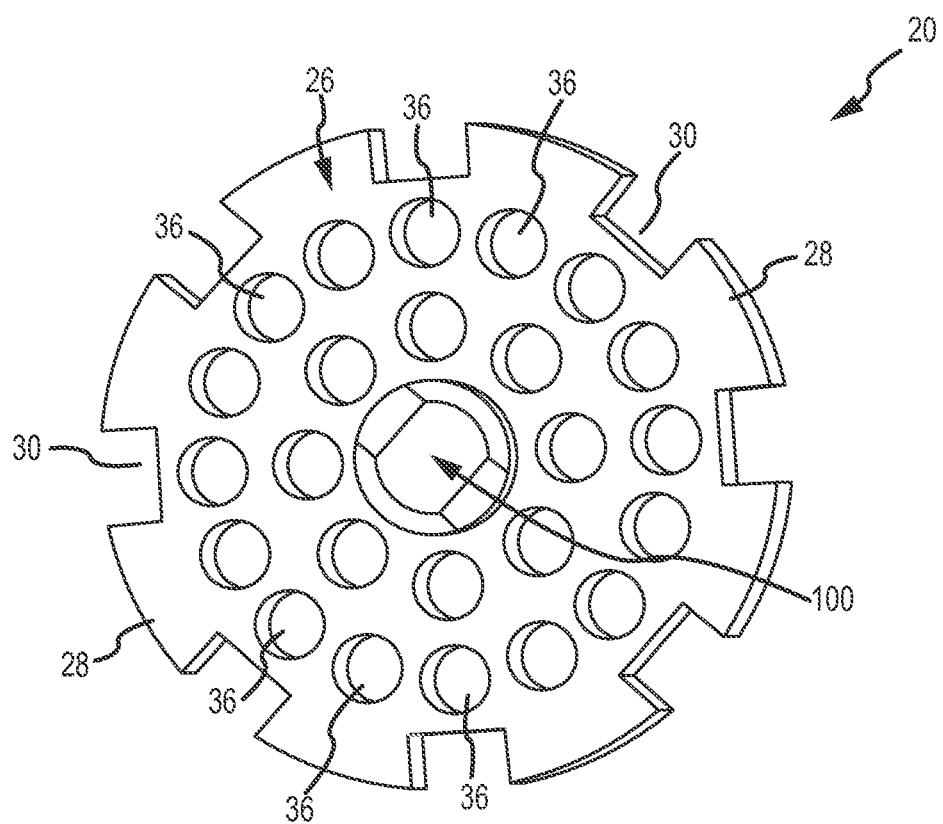
FIG. 5 is a top view of the exemplary cryogenic sample holder of FIG. 1 without the cap or pin.
Figure 6:
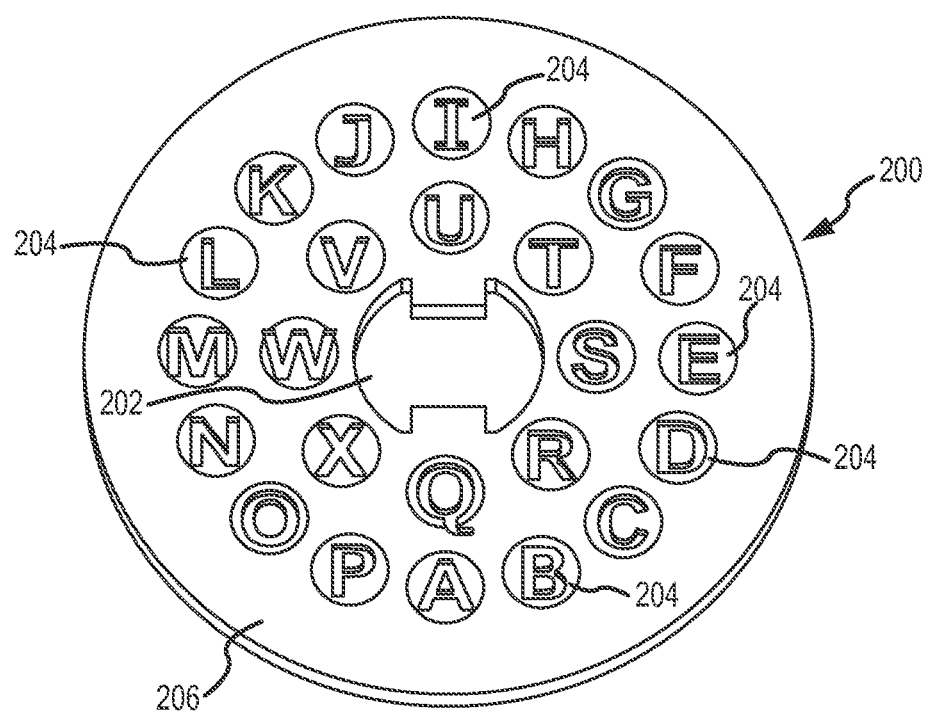
FIG. 6 is a top view of a cap used with an exemplary cryogenic sample holder according to aspects of the invention.
Figure 7:
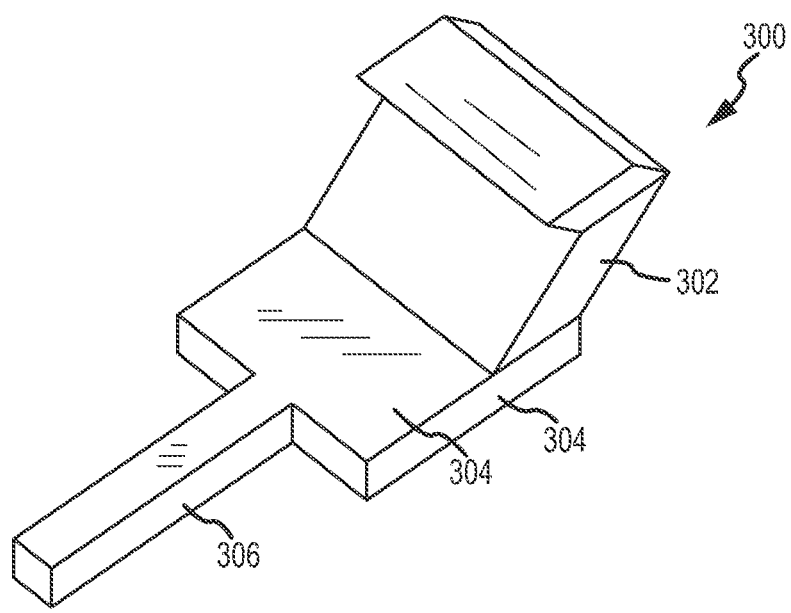
FIG. 7 is a side perspective view of an exemplary pin used with a cryogenic sample holder in accordance with one or more aspects of the present disclosure.

A cap 200 is preferably circular so as to align with the generally circular shape of the portion of top surface 26 that includes openings 36, but can be of any suitable shape. Cap 200 is preferably formed of the same material as body 20 although it can be formed of any suitable material. A central opening 202 is formed in cap 200 and is configured to receive second end 102 of stem 100, as shown in FIGS. 3 and 4. Because of the configuration of opening 202 it fits over end 102, but will not move past the cylindrical portion of stem 100 beneath end 102. Cap 200 in this embodiment has indicia 204 on its top surface 206, as best seen in FIG. 6. The purpose of indicia 204 is to identify which biological specimens are retained in the BSSD immediately below the indicia. This makes it simpler for users to identify biological specimens.

A pin 300 is used to affix cap 200 to stem 100 by positioning pin in opening 104, as best seen in FIG. 4. Pin 300 has a handle portion 302, a flat body 304, and an insert 306. The handle portion 302 is for a user to easily remove or insert pin 300. Flat body portion 304 has a relatively broad surface area to apply pressure to a relatively large surface area of cap 200 in order to help retain cap 200 in a flat position. Insert 306 is retained in opening 104 to maintain cap 200 in place. Pin 300 can be made of any suitable material and be of any suitable shape.

Figure 8:
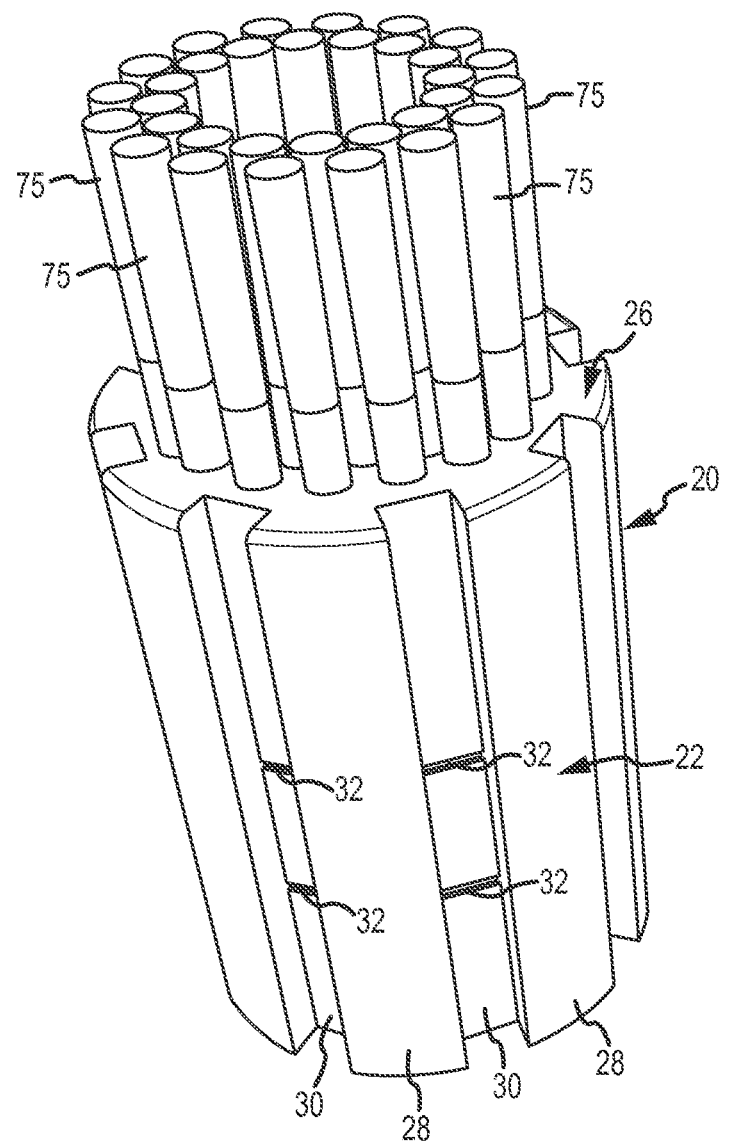
FIG. 8 is a side perspective view of an exemplary cryogenic sample holder according to the invention showing BSSDs inserted into openings in the holder.

Turning to FIG. 8, body 20 is shown with BDDSs 75 in the openings 36. BDDSs are known in the art and can be of any suitable structure. The openings 36 preferably have a diameter of no greater than 0.1 mm to 0.5 mm greater than the BDDSs, or no greater than 0.1 mm greater than the BDDSs. The purpose of these dimensions is to help prevent the BDDS, and the biological specimen each contains, from being shaken or tossed about during shipping.

While not shown here, each BDDS 75 is inserted into an opening 36 until it reaches the bottom, or any other stopping point built into an opening 36. Each BDDS 75 preferably includes a biological specimen at its lower tip. When a BDDS 75 is inserted into an opening 36 and cryogen is in inner cavity 34, the lower tip of BDDS 75 and the biological specimen are immersed in the cryogen and the biological specimen is maintained at roughly the temperature of the cryogen, which should be below the glassification temperature of the specimen. The cryogen may or may not directly contact the specimen.

When each BDDS 75 to be transported is inserted into an opening 36 (it being understood that not every opening 36 need have a BDDS 75, and holder 10 can be shipped only partially full), cap 200 is placed on stem 100 and pin 300 is inserted into opening 104 to maintain cap 200 in place and help prevent each BDDS 75 from moving.

While being shipped, holder 10 is placed in a container that includes cryogen, and the cryogen enters inner cavity 34 through openings 32 as previously described.

Holder 10 can be removed from a container by placing a bar or hook through opening 106 and lifting and moving holder 10. Because of its insulating properties and because it preferably retains some cryogen when removed from the container, holder 10 can retain biological specimens at their proper temperature for up to 1-5 minutes, and possibly longer.

FIGS. 10-13 show an alternate embodiment of the invention. In this embodiment cryogen enters an enclosed container, flows upward through one or more tubes, and exits one or more openings in the tubes to enter the open top of an adjacent tube of lower height and fill it at least partially with cryogen. A BSSD is positioned in the tube of lower height and the biological specimen in the BSSD is immersed in the cryogen.

Figure 10:
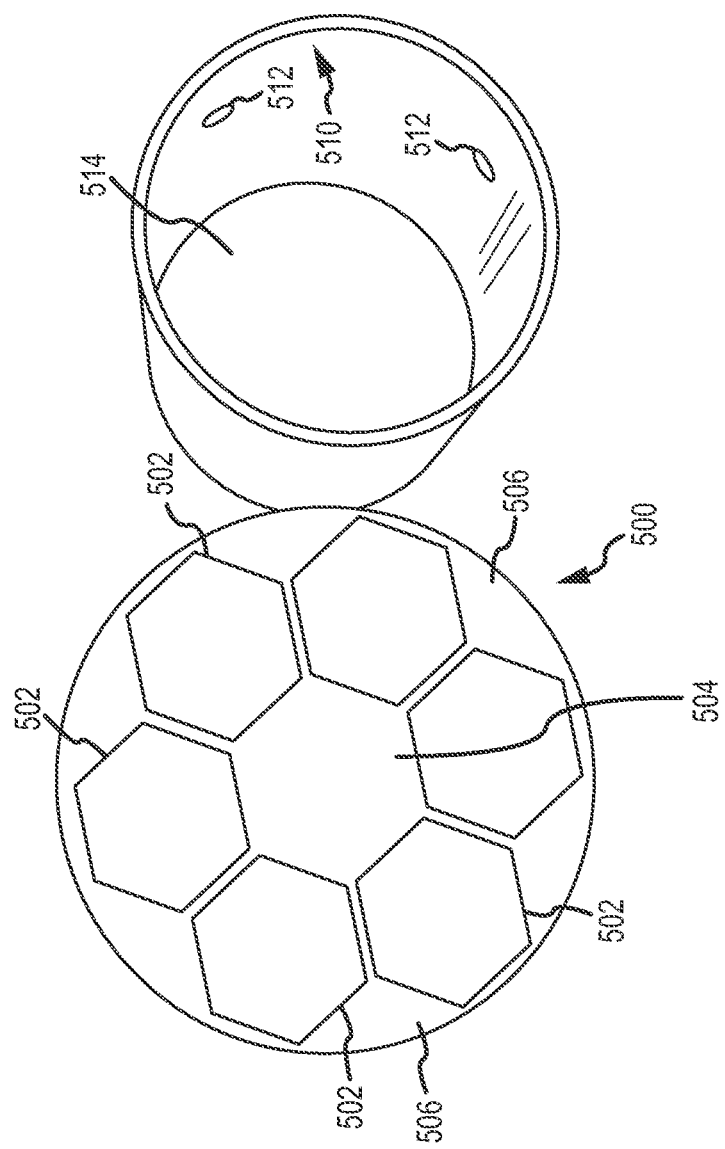
FIG. 10 is a top view of an alternate embodiment of the present disclosure.

FIG. 10 is a top view of the bottom portion 500 and top portion 510 of a container according to this aspect of the invention. This container is preferably cylindrical, relatively thin and can be comprised of any of the previously mentioned plastics. Bottom portion 500 includes one or more tall tubes 502 and, in this embodiment, a single short tube 504. All of the tubes 502 and 504 are preferably comprised of a suitable plastic and can be of any suitable shape, although as shown they are hexagonal.

Figure 11:
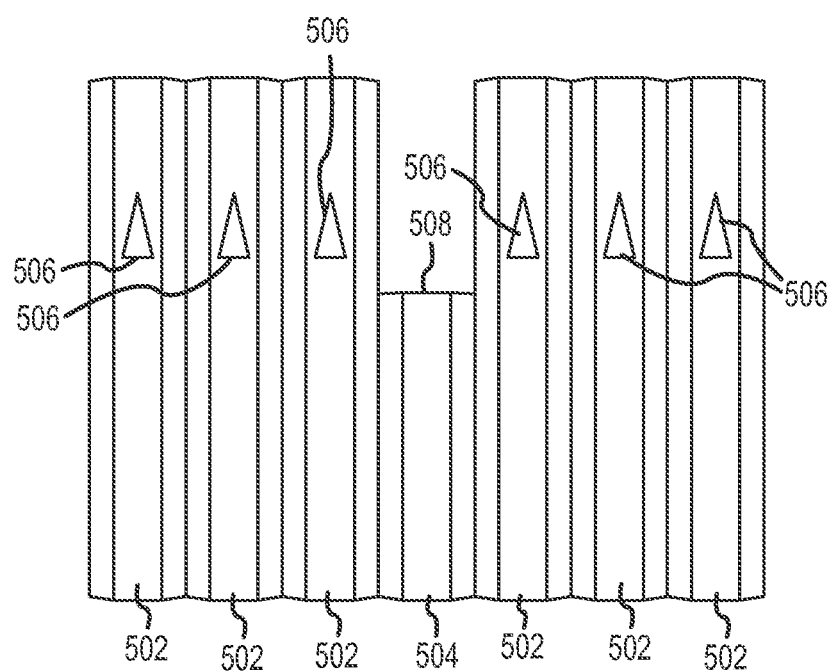
FIG. 11 is a side view of tubes that may be used in the embodiment of FIG. 10.
Figure 12:
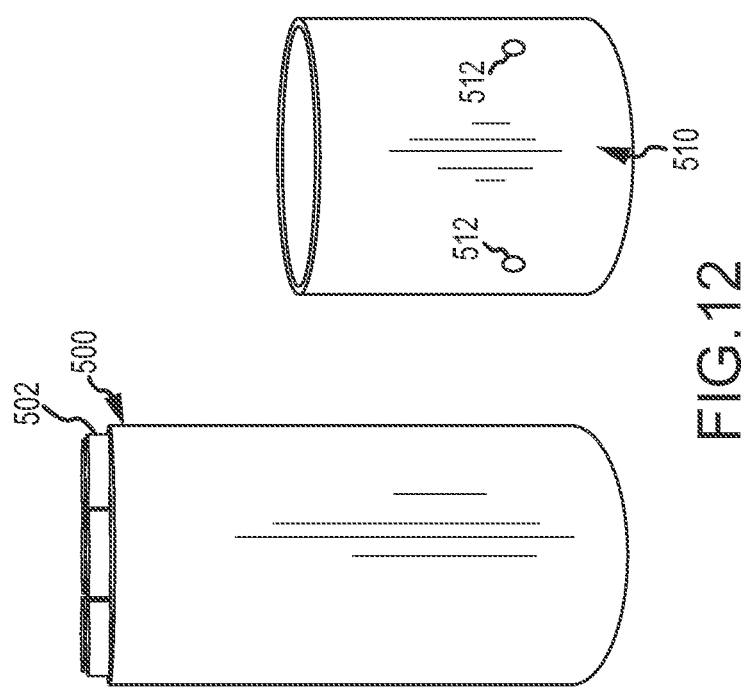
FIG. 12 is a side view of the embodiment shown in FIG. 10.
Figure 13:
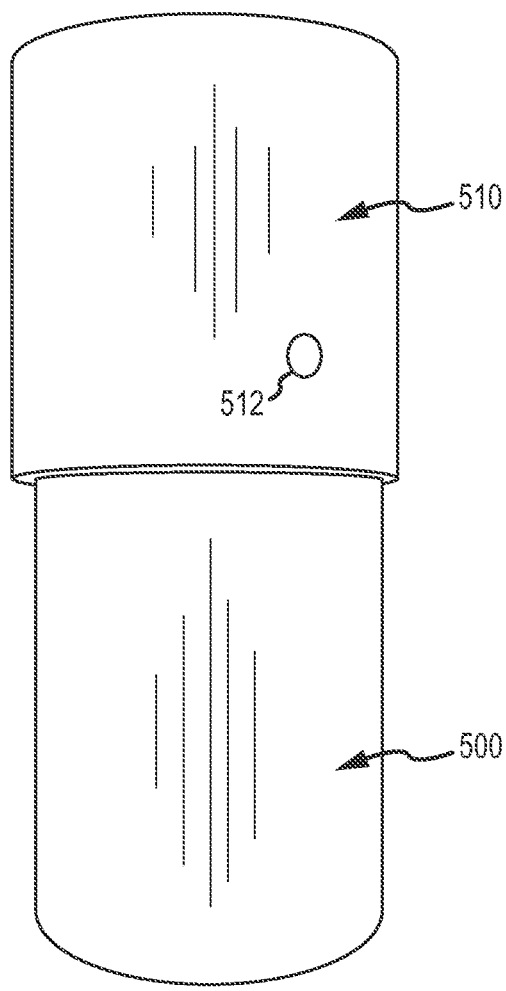
FIG. 13 is a side view of the embodiment of FIG. 10 fully assembled.

Each tube 502 has an open bottom and an opening 506 that is higher than the open top 508 of short tube 504. This is best seen in FIG. 11, where the tubes have been removed from bottom portion 500. When the tubes 502 and 504 are assembled into a container comprising bottom portion 500 and top portion 510, as shown in FIG. 13, the container is immersed in cryogen. The cryogen enters the bottom surface of bottom portion 510 through openings (not shown) and as the container is pushed deeper into the cryogen, the cryogen level moves up from the bottom of tubes 504, exits openings 506 and flows into open top 508 of tube 504 (the bottom of tube 504 is closed so cryogen cannot enter from the bottom).

Optionally, there is a soft, cushioning material 506, such as cotton, between tubes 502 and the wall of bottom portion 500 to ensure a snug fit.

Top portion 510 may also include a soft, cushioning material 516, such as cotton, which further ensures that a BDDS in tube 502 will be snug in the container and not be very prone to movement or breakage.

Figure 14:
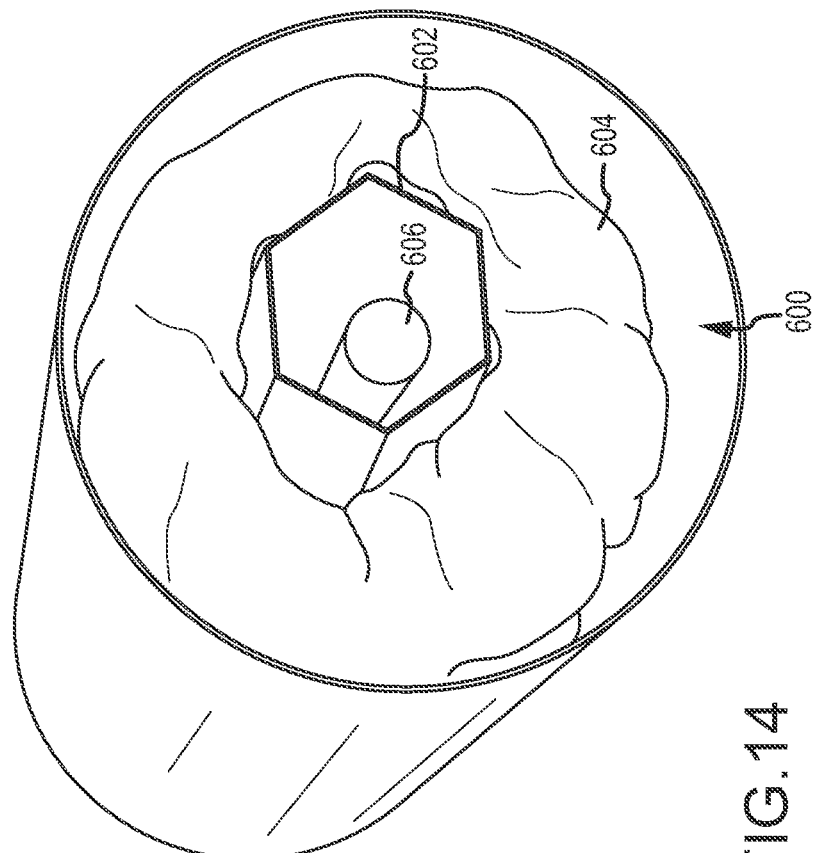
FIG. 14 is a top view of an alternate embodiment of the present disclosure.
Figure 14:
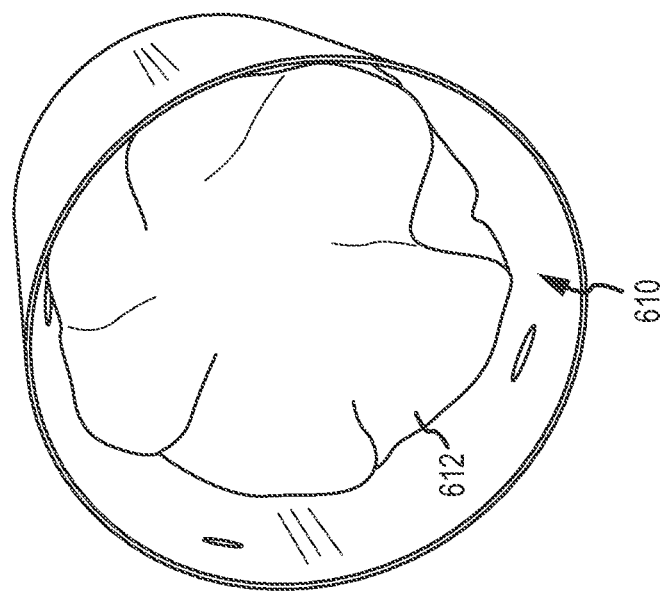
Figure 15:
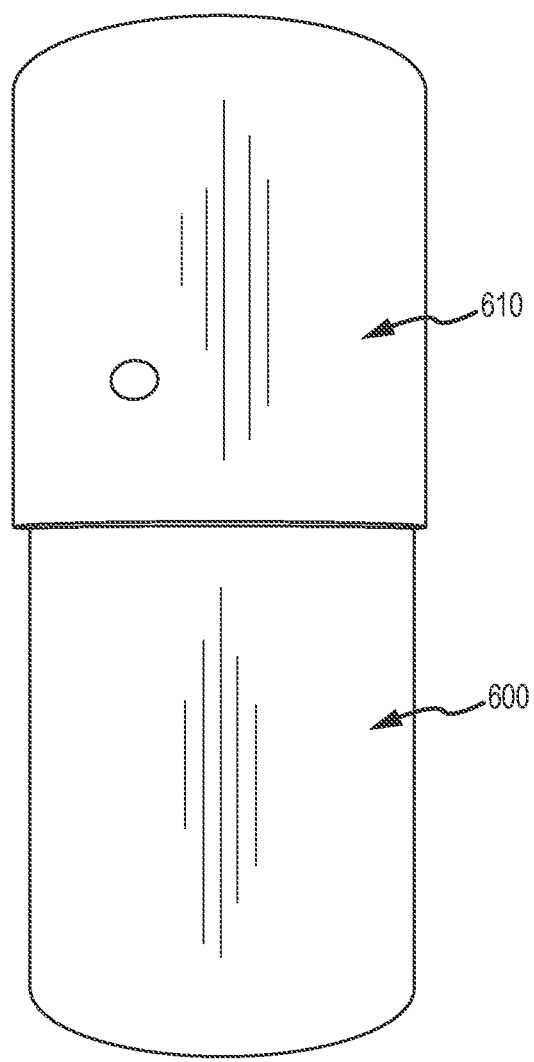
FIG. 15 is a side view of the embodiment of FIG. 14 fully assembled.

FIGS. 14 and 15 show an alternate embodiment of a holder. This holder includes a lower portion 600 and an upper portion 610. Lower portion 600 houses a tube 602 that retains a BDDS 606. Preferably tube 602 is surrounded by a soft, cushioning material 604, which could be cotton. Further, material 604 could be inside of tube 602 to help retain BDDS 606 in position and to absorb cryogen to keep the biological specimen cold.

Upper portion 610 also preferably has a soft, cushioning material 612, which may be cotton.

In operation, BDDS 606 is placed in tube 602, into which cryogen is placed. Then upper portion 610 is positioned over and secured to lower portion 600, as shown in FIG. 15. If cushioning material 612 is used, it helps to further secure BDDS 606 in the assembled container.

Some exemplary combinations of elements of the invention are as follows:

1. A cryogenic biological sample holder comprising:
    (a) one or more openings, wherein each opening is for retaining a biological sample support device (BSSD); and
    (b) an insulating material at least ¼" thick surrounding the BSSD.
2. The sample holder of example 1 that includes a plurality of openings, wherein each of the plurality of openings is for retaining a separate BSSD.
3. The sample holder of example 2 wherein at least one of the plurality of openings is cylindrical.
4. The sample holder of example 3 wherein each of the cylindrical openings has a diameter of between 0.5 mm to 10 mm.
5. The sample holder of example 2 wherein at least one of the plurality of openings is not cylindrical.
6. The sample holder of any of examples 1-5 that further includes a biological sample retained in the BSSD.
7. The sample holder of either example 3 or 4 wherein the opening is no greater than 0.1 mm in diameter than the BSSD.
8. The sample holder of either example 3 or 4 wherein the opening is no greater than 0.3 mm in diameter than the BSSD.
9. The sample holder of any of examples 1-8 wherein the openings have a diameter no greater than 0.1 mm to 0.5 mm than the diameter of the BSSD received in the opening.
10. The sample holder of any of examples 1-8 wherein the openings have a diameter of no greater than 0.1 mm to 0.3 mm than the diameter of the BSSD received in the opening.
11. The sample holder of example 2 that has at least ten openings, each of the openings for retaining a BSSD.
12. The sample holder of example 11 wherein each opening retains a BSSD.
13. The sample holder of example 1 that has at least twenty openings, each of the openings for retaining a BSSD.
14. The sample holder of example 13 wherein each opening retains a BSSD.
15. The sample holder of any of examples 1-14 that comprises a body portion that includes the openings.
16. The sample holder of any of examples 1-15 that includes a body portion having a top surface and a stem extending upwards from the top surface.
17. The sample holder of any of examples 1-16 that includes a cap for holding the BSSD in each opening in which a BSSD is retained.
18. The sample holder of example 16 that includes a cap for retaining each BSSD in the opening in which it is retained, wherein the cap fits over and is affixed to the stem.
19. The sample holder of example 18 wherein the cap has an opening that fits onto the top of the stem.
20. The sample holder of example 19 wherein the stem has a lower opening for receiving a pin in order to affix the cap to the stem.
21. The sample holder of any of examples 16-20 wherein the stem has an upper opening used for lifting and transporting the sample holder.
22. The sample holder of example 21 wherein the stem has an upper opening used for lifting and transporting the sample holder, the second aperture being above the first aperture.
23. The sample holder of any of examples 17-20 wherein the cap includes indicia to identify each biological specimen retained beneath the cap, wherein each indicia aligns with the BSSD beneath the indicia to identify the biological specimen in the BSSD.
24. The sample holder of any of examples 1-23 wherein the body has an exterior surface and includes vertical channels on the exterior surface, the vertical channels including openings leading to an inner cavity of the body, the openings to permit cryogen to pass into the inner cavity.
25. The sample holder of example 24 that includes vertical projections adjacent each vertical channel wherein the projections provide insulation.
26. The sample holder of example 25 wherein each vertical projection is solid.
27. The sample holder of example 24 wherein each vertical projection is hollow.
28. The sample holder of example 27 wherein each vertical projection includes an interior opening in communication with the inner cavity and partially fills with cryogen when cryogen is introduced to the inner cavity.
29. The sample holder of any of examples 1-23 that includes a generally smooth outer surface and openings in the outer surface, the openings leading to an inner cavity in the body and permitting cryogen to pass into the inner cavity.
30. The sample holder of any of examples 1-28 that includes an inner cavity for retaining cryogen and dimensioned such that the biological sample retained by each BSSD is immersed in the cryogen when the BSSD is retained in an opening.
31. The sample holder of any of examples 1-31 wherein each opening extends into the cavity.
32. The sample holder of example 31 wherein the BSSD is closed so that cryogen cannot directly contract a biological specimen within the BSSD.
33. The sample holder of example 31 wherein the BSSD is open so that cryogen can directly contact a biological specimen within the BSSD.
34. The sample holder of example 31 wherein each opening is closed so cryogen cannot enter it.
35. The sample holder of example 31 wherein each opening has an opening near the bottom so that cryogen can enter it.
36. The sample holder of example 32 wherein the opening is at the bottom of the BSSD.
37. A sample holder that has sufficient thermal mass to keep biological specimens below the glassification temperature of the biological specimen for at least five minutes.
38. A sample holder that maintains a biological specimen below its glassification temperature for at least one minute.
39. A sample holder that maintains a biological specimen below its glassification temperature for at least 1-5 minutes.

40. The sample holder of any of examples 1-39 that can utilize either gaseous or liquid cryogen.
41. The sample holder of any of examples 1-40 that is comprised of plastic.
42. The sample holder of any of examples 1-40 that is comprised of one of the group consisting of (a) polypropylene, (b) polyethylene, and (c) polyvinyl chloride.
43. The sample holder of any of examples 1-42 wherein the body, stem, pin and cap are all formed of the same material.
44. The sample holder of any of examples 1-43 wherein the biological sample is an embryo.
45. The sample holder of any of examples 1-43 wherein biological sample is an unfertilized human egg.
46. The sample holder of any of examples 1-45 that further includes an absorbent material in one or more openings for absorbing cryogen.
47. The sample holder of any of examples 1-46 that further includes an absorbent material in the inner cavity to absorb cryogen.
48. A cryogenic vessel including cryogen and the sample holder of any of examples 1-47.
49. A sample holder that has an exterior container and interior tubes wherein a shorter tube has a closed bottom and a top opening, is surrounded by taller tubes that have bottom openings and an aperture above the top opening in the shorter tube; and the container has a bottom surface with openings therein to permit the passage of cryogenic fluid therethrough, and through the bottoms of the taller tubes, and through the apertures in the taller tubes and into the top opening in the shorter tube.
50. The sample holder of example 49 that includes soft packing filler in the tube that retains the samples.
51. The sample holder of example 50 wherein the soft packing is cotton.

The foregoing description is provided to enable any person skilled in the relevant art to practice the various embodiments described herein. Various modifications to these embodiments, however, will be readily apparent to those skilled in the relevant art. Thus, the claims are not limited to the embodiments shown and described herein, but are to be accorded the full scope consistent with their language, wherein reference to an element in the singular is not intended to mean "one and only one" unless specifically stated, but rather "one or more." All structural and functional equivalents to the elements of the various embodiments described throughout this disclosure are meant to be covered by the claims and the legal equivalents thereof.

What is claimed is:

1. A cryogenic biological sample holder comprising:
   a body comprising insulating material, a top surface, an inner cavity, and an exterior surface, the top surface comprising one or more openings, wherein each of the one or more openings is configured to retain a biological sample support device (BSSD), the inner cavity for retaining cryogen, wherein the insulating material is at least ¼" thick surrounding the BSSD, and the exterior surface comprising vertical channels comprising openings leading to the inner cavity of the body, the openings to permit cryogen to pass into the inner cavity;
   vertical projections adjacent to the vertical channels wherein the vertical projections provide insulation, are hollow, and comprise an interior opening in communication with the inner cavity; and
   a stem extending upwards from the top surface.

2. The sample holder of claim 1 wherein each of the one or more openings is for retaining a separate BSSD.
3. The sample holder of claim 2 wherein at least one of the one or more openings is cylindrical.
4. The sample holder of claim 3 wherein each of the cylindrical openings has a diameter of between 0.5 mm to 10 mm.
5. The sample holder of claim 3 wherein at least one of the one or more openings is no greater than 0.1 mm in diameter than the BSSD.
6. The sample holder of claim 3 wherein at least one of the one or more openings is no greater than 0.3 mm in diameter than the BSSD.
7. The sample holder of claim 2 wherein at least one of the one or more openings is not cylindrical.
8. The sample holder of claim 2 comprising at least ten openings, each of the at least ten openings configured to retain a BSSD.
9. The sample holder of claim 8 wherein each of the at least ten openings retains a BSSD.
10. The sample holder of claim 1 further comprising a biological sample retained in the BSSD.
11. The sample holder of claim 1 wherein each of the one or more openings has a diameter no greater than 0.1 mm to 0.5 mm than the diameter of the BSSD received therein.
12. The sample holder of claim 1 wherein each of the one or more openings has a diameter of no greater than 0.1 mm to 0.3 mm than the diameter of the BSSD received therein.
13. The sample holder of claim 1 further comprising a cap for retaining each BSSD in the opening in which it is retained, wherein the cap fits over and is affixed to the stem.
14. The sample holder of claim 13 wherein the cap further comprises indicia to identify one or more biological specimens retained beneath the cap, wherein each of the indicia aligns with the BSSD beneath the indicia to identify the biological specimen in the BSSD.
15. The sample holder of claim 1 wherein each vertical projection is solid.
16. The sample holder of claim 1 wherein each BSSD includes a biological specimen, and the inner cavity is dimensioned such that the biological specimen retained by each BSSD is immersed in the cryogen when the BSSD is retained in an opening.
17. The sample holder of claim 1 wherein the body comprises a side surface and openings in the side surface, wherein at least some of the openings extend into the inner cavity to permit cryogen to enter the inner cavity.
18. The sample holder of claim 17 comprising a cryogenic vessel comprising cryogen.
19. The sample holder of claim 1 that has sufficient thermal mass to keep a biological specimen below the glassification temperature of the biological specimen for at least five minutes.
20. The sample holder of claim 1 that is comprised of plastic.
21. The sample holder of claim 1 that is comprised of one of the group consisting of (a) polypropylene, (b) polyethylene, and (c) polyvinyl chloride.
22. The sample holder of claim 1 further comprising an upper portion and a lower portion, the lower portion which comprises the BSSD that retains the samples.
23. The sample holder of claim 22 wherein the upper portion is secured to the lower portion.

* * * * *